United States Patent
Roos et al.

[19]

[11] Patent Number: 6,075,837
[45] Date of Patent: Jun. 13, 2000

[54] IMAGE MINIFYING RADIOGRAPHIC AND FLUOROSCOPIC X-RAY SYSTEM

[75] Inventors: Pieter Gerhard Roos, Bainbridge, Ohio; Paul M. Stivender, Oconomowoc, Wis.

[73] Assignee: Picker International, Inc., Highland Heights, Ohio

[21] Appl. No.: 09/044,424

[22] Filed: Mar. 19, 1998

[51] Int. Cl.[7] .................................................. H05G 1/64
[52] U.S. Cl. ........................................... 378/98.2; 378/62
[58] Field of Search ...................................... 378/98.2, 62

[56] References Cited

U.S. PATENT DOCUMENTS

| | | | |
|---|---|---|---|
| 4,833,625 | 5/1989 | Fisher et al. | 378/98.2 |
| 5,146,485 | 9/1992 | Schweichler et al. | 378/196 |
| 5,327,474 | 7/1994 | Inoue et al. | 378/20 |
| 5,608,774 | 3/1997 | Policher et al. | 378/98.8 |
| 5,912,943 | 6/1999 | Deucher et al. | 378/98.8 |

OTHER PUBLICATIONS

"Storage–phosphor–based Digital Mammography Using a Low–Dose X–ray System Optimized for Screen–Film Mammography", Jennings, et al. SPIE V. 2708 220–231.

*Primary Examiner*—Craig E. Church
*Attorney, Agent, or Firm*—Fay, Sharpe, Fagan, Minnich & McKee, LLP

[57] ABSTRACT

An x-ray source assembly (28) includes an x-ray tube with an adjustably sized focal spot (22) for fluoroscopic viewing and radiographic recording. The x-ray source is spaced from an object to be imaged by a first distance (q). An x-ray image receptor assembly is position at a second distance (p-q) away from the object to be imaged. The second distance is greater than or equal to the first distance. A system (40) minifies electronic images from an image receptor (24) for fluoroscopic viewing and radiographic and cineradiographic image recording to a size that is approximately the size of the object being imaged. In this manner, the displayed images have a level of perceived detail that is substantially equal to images generated from radiation receptors positioned contiguous to the subject.

20 Claims, 3 Drawing Sheets

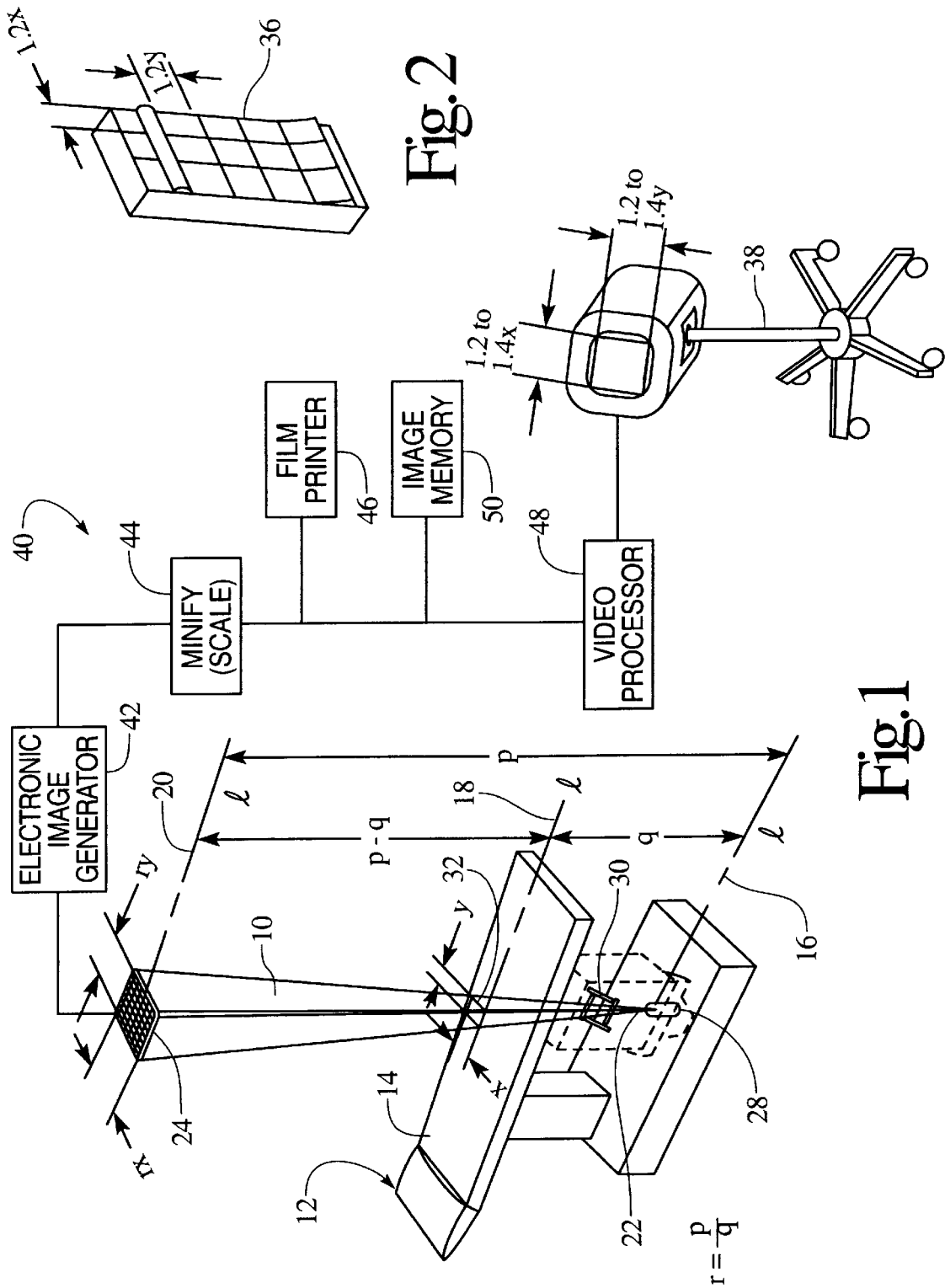

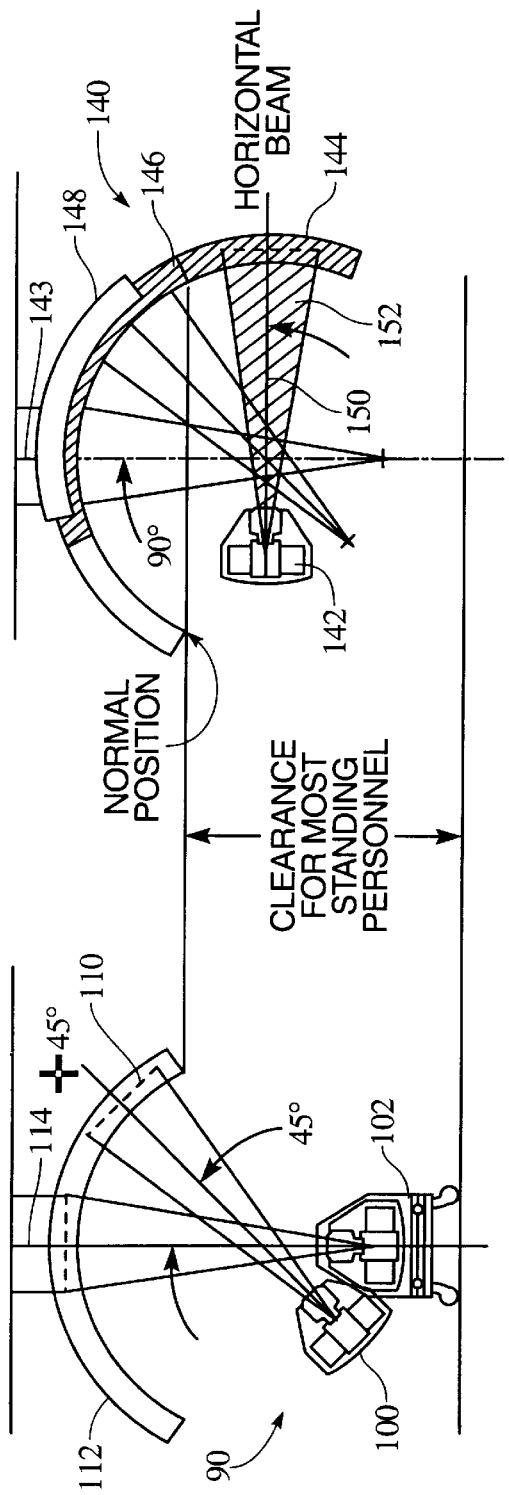
Fig. 5
Fig. 4
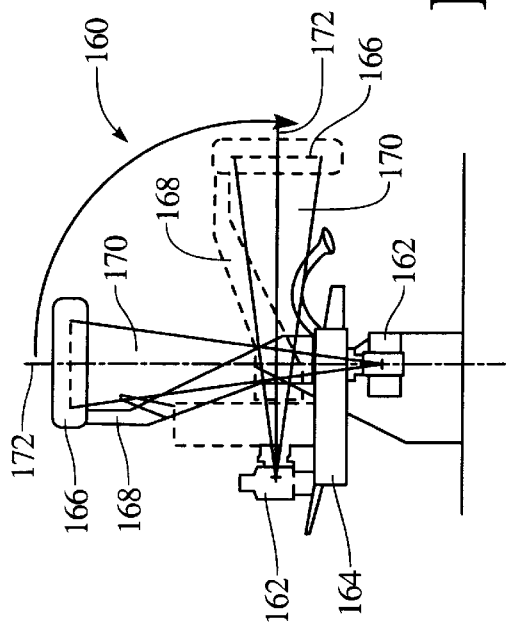
Fig. 6

IMAGE MINIFYING RADIOGRAPHIC AND FLUOROSCOPIC X-RAY SYSTEM

BACKGROUND OF THE INVENTION

The present invention relates to the medical diagnostic imaging arts. It finds particular application in conjunction with a clinical medical radiographic and fluoroscopic x-ray system and will be described with particular reference thereto. However, it should be appreciated that the present invention may also find application in conjunction with other types of imaging systems and applications.

Sepsis control and access to the full perimeter of the patient are two prime requirements for surgical and interventional procedures performed in, but not limited to, hospital operating rooms, health care facilities that utilize minimally invasive surgical technology, and in dental operatories. The above requirements have almost always compromised the convenience of use and the imaging performance delivered from classical surgical "C-Arm" x-ray systems, both fixed and mobile.

In particular, traditional x-ray systems are designed to be used with the x-ray image receptor positioned as close as is practical to the patient's skin. Traditional systems using cassettes and intensifiers typically demonstrate 1 to 2 line pairs per millimeter (lp/mm) fluoroscopic spatial resolution at a dose rate of 10 to 30 nGy (~1 to 3 µR) per video frame at the entrance of the image receptor for x-ray tube focal spots measuring between 0.5 and 0.9 mm. Substituting a flat plate matrix imager and using the traditional x-ray geometry results in about the same performance when these devices are fully developed. The spatial resolution for high photon flux radiographic recording of fluoroscopic images is typically between 3 to 5 lp/mm.

The traditional viewing or recording film image magnification ratio as it relates to the anatomy of interest is typically 1.2 to 1.4:1. If the traditional receptor is moved away from the patient's skin, the magnification ratio increases and this disadvantageously causes the always-present penumbral unsharpness to be magnified to the point where subtle anatomic margins begin to disappear. Another consequence of moving the traditional receptor some distance away is the reduced amount of patient anatomy that can be captured at the receptor.

In a known highly-specialized application that is used specifically for imaging the relatively small field size associated with a mechanical heart valve, a "microfocus" x-ray source is employed to project images on an image intensifier located at a great distance away from the patient. The "microfocus" source is utilized to prevent unsharpness in the magnified image. The sole purpose of magnifying the image of the heart valve is to permit assessment of its mechanical integrity, specifically the detection of small cracks in the welding that are more easily seen using magnification. This specialized imaging system demonstrates the well-known limitations in kilowattage presented by all microfocus x-ray tube designs where the finite melting point of tungsten anodes effectively eliminates having practical and affordable stop-motion microfocus magnification radiography in clinical settings.

Accordingly, it has been considered desirable to develop a new and improved image minifying radiographic and fluoroscopic x-ray system which meets the above-stated needs and overcomes the foregoing difficulties and others while providing better and more advantageous results.

SUMMARY OF THE INVENTION

In accordance with one aspect of the present invention, a diagnostic imaging system is disclosed. The imaging system includes an x-ray tube source spaced from an object to be imaged by a first distance. An image receptor is positioned at a second distance away from the object to be imaged remote from the x-ray tube. The second distance is greater than the first distance. A mechanism is provided for minifying projected image patterns received by the image receptor to a size that is approximately the size of the object being imaged.

In accordance with a second aspect of the present invention, a method of diagnostic imaging is disclosed. The method includes spacing an x-ray tube from an object to be imaged by a first distance, positioning an image receptor a second distance away from the object to be imaged remote from the x-ray tube, the second distance being greater than the first distance, and minifying projected image patterns received by the image receptor to a size that is approximately the size of the object being imaged.

In accordance with a third aspect of the present invention, a method of diagnostic imaging is disclosed wherein a beam of radiation is projected a first distance $D_1$ from a focal spot to a plane of a region of interest of a subject, and a second distance $D_2$ from the region of interest plane to a conversion plane on which the radiation beam is converted into an electronic image representation. The electronic image representation is converted into a human readable display. The method further includes the distance $D_2$ being at least as large as $D_1$ such that each transverse dimension of the radiation beam at the conversion plane is $(D_1+D_2)/D_1$ as big as at the region of interest plane, reducing the electronic image representation by between $D_1/(1.0(D_1+D_2))$ and $D_1/(1.5(D_1+D_2))$ such that each dimension of the human readable display is 1.0 to 1.5 times as large as corresponding structure intersected by the beam in the region of interest plane.

The image minifying radiographic and fluoroscopic x-ray system of the present invention includes an x-ray source assembly equipped with an x-ray tube having a plurality of selectable sized focal spots as appropriate for fluoroscopic viewing and for radiographic recording at elevated radiation fluence rates consistent with motion stopping radiography and cineradiography when recording said fluoroscopically viewed images. The source assembly is also equipped with a beam collimating device to control the size of a rectangular or circular projected x-ray beam. The source assembly is placed away from the object being examined by a distance consistent with or identical to the distance commonly employed to minimize the radiation fluence to the object while conserving the motion stopping capabilities. An x-ray image receptor assembly is placed to intercept the x-ray beam and is set at a distance from the imaged object by a distance that is equal to or exceeds the distance from the focal spots to the object image plane. The receptor assembly is equipped with known electronic means to immediately and simultaneously minify the projected image patterns to a size for fluoroscopic viewing and radiographic or cineradiographic image recording that is approximately the size of the object being examined so as to render the displayed image patterns at a level of perceived detail that is equal to those non-minified images commonly acquired using x-ray receptors that are commonly positioned as close as is practical to the object being examined.

The large distance between the object image plane and the receptor assembly is necessary or often useful in gaining access to the patient. Further, the large distance can be useful for preserving sepsis control by eliminating the need to drape the image receptor assembly with sterile materials. The large distance is also useful in preventing obstructive interference with operating room lights and other apparatus that is used adjacent to or above the patient.

Thus, imaging application conflicts experienced in procedure rooms that use classical x-ray systems for surgical interventional imaging procedures can be resolved by moving the x-ray image receptor away from the operative site. The optimum location for the remotely located receptor assembly is approximately defined by the space commonly used for positioning the classical overhead operating room light sources.

One advantage of the present invention is the provision of an image minifying radiographic and fluoroscopic x-ray system having a flat panel image receptor and an x-ray source positioned so as to provide a 1:3 magnification ratio and provide viewed and filmed images at a conventional 1.2 to 1.4:1 ratio.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiments and are not to be construed as limiting the invention.

FIG. 1 is a perspective view of an image minifying radiographic and fluoroscopic X-ray system which incorporates features of the present invention therein;

FIG. 2 is a perspective view of an exemplary radiography viewing device of the image minifying radiographic and fluoroscopic x-ray system of FIG. 1;

FIG. 4 is an end view of the image minifying radiographic and fluoroscopic x-ray system of FIG. 3;

FIG. 5 is a third embodiment of an image minifying radiographic and fluoroscopic x-ray system which incorporates features of the present invention therein; and FIG. 6 is a fourth embodiment of an image minifying radiographic and fluoroscopic x-ray system which incorporates features of the present invention therein.

DETAILED DESCRIPTION OF THE PREFERRED EMBODIMENT(s)

Figure 3:
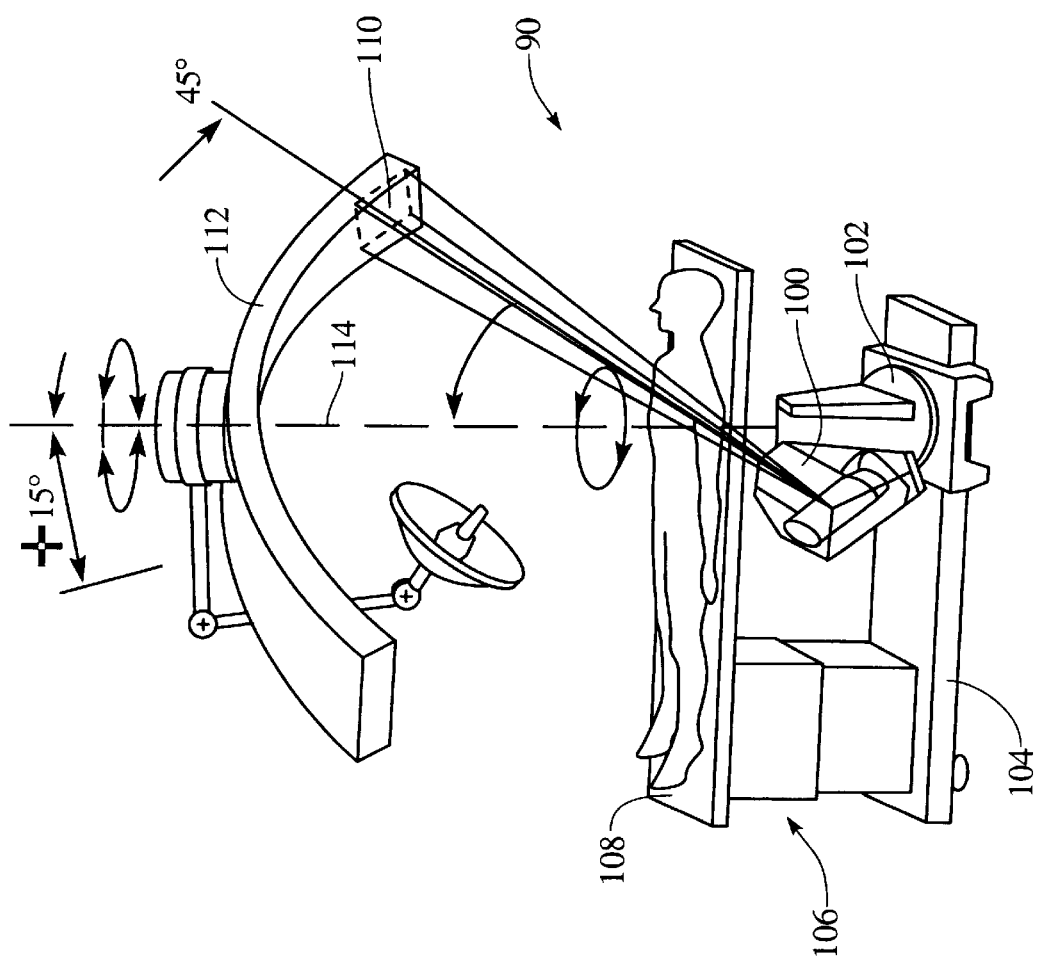
FIG. 3 is a perspective view of a second embodiment of an image minifying radiographic and fluoroscopic x-ray system which incorporates features of the present invention therein.

With reference to FIG. 1, an x-ray beam 10 is set within a surgical table 12 having a radiolucent table surface 14 in a region where a surgical intervention is to be performed. In the embodiment being described, a vertical x-ray beam geometry is illustrated, however, it should be appreciated that the present invention is equally applicable to horizontal beam geometries, canted beam geometries and the like.

Reference lines 16, 18, and 20 define horizontal geometric planes corresponding to a focal spot 22, an operating image plane of interest (typically set at 20 cm above the table surface 14), and a flat plate image receptor 24, respectively. These planes establish the dimensions or distances p between the source and the receptor and q between the source and the plane of interest. An acquisition magnification ratio r is defined by r=p/q. An x-ray source 28, such as a rotating anode-type x-ray tube, includes a variable size beam aperture collimator 30 that is adjusted to vary the cross section of the radiation beam 10. An imaging area 32 within a patient is defined at the intersection of the x-ray beam and the plane of interest located by line 18.

The flat plate image receptor 24 is positioned at a distance p-q from the plane of interest identified by line 18. The flat plate x-ray image receptor 24 constitutes the input component to an image processing subsystem 40. The active area of the flat plate image receptor 24 is an area defined by rx and ry which are products of the magnification ratio r and the dimensions x and y which define two sides of the imaging area 32 when the beam-defining collimator 30 is opened to a maximum.

The remainder of the image processing subsystem 40 includes means for assembling and transmitting the acquired image. In particular, the system 40 can employ scan converters for the image data so as to, for example, transmit the assembled images to a laser transparency printer(s) for radiographic recording, or to electronically store the media for archival purposes. The radiographic images that have been transferred to film can be displayed on a radiography viewing device such as a light box 36 (FIG. 2). In addition, fluoroscopy image sequences are sent to a video monitor(s) 38.

The displayed images are minified to the sizes of traditional magnification ratios (typically 1.2 x to 1.4 x and 1.2 y to 1.4 y) with respect to the anatomy. That is, the images are reduced to the conventional scale for radiographic images to enable conventional measurements to be used when analyzing the film. Alternatively, the minification can be adjusted to attain a ratio of 1:1 with the anatomy to allow direct measurement. Thus, the final output images, originally acquired in the magnified state, can be minified for display at the same traditional sizes with effective magnification ratios in the range of about 1.0 x to about 1.5 x, and about 1.0 y to about 1.5 y, and preferably, about 1.2 x to about 1.4 x, and about 1.2 y to about 1.4 y, with respect to the anatomy.

In the preferred embodiment, the system 40 includes an electronic image generator 42 which converts the output of the flat screen into an electronic image representation that is rx by ry in size, where r=p/q. A minifying processor 44 scales the electronic image by a scaling factor between 1.2 (q/p) and 1.4 (q/p). That is, the electronic image is reduced by between p/(1.2 q) and p/(1.4 q). A film printer 46 prints the electronic image onto an x-ray film for display on the light box 36. A video processor 48 formats the minified image into approximate format for display on the video monitor 38. A digital memory device 50 stores minified electronic images for later display.

In the illustrated embodiment, a magnification ratio in the range of 1:2.6 to 1:3 is utilized between the anatomy and the detected image in plane 20. Further, the flat plate image receptor 24 is an amorphous silicon-based flat panel x-ray detector having length and width dimensions that measure about three times the maximum dimensions (x, y) of the perimeter of the operative imaging plane 32 within the patient. Suitable amorphous silicon-based flat panel x-ray detectors are described in U.S. Pat. Nos. 5,079,426; 5,117,114; 5,164,809; 5,262,649.

The flat panel x-ray detector provides benefits in terms of cost as well as dose utilization efficiency by employing pixel elements that are set in a pixel matrix pitch that is three times greater than the very small pixel matrix pitch that would be required if the flat plate imager were to be used in the traditional acquisition geometry.

The inverse square law for divergent beams cancels out because the image receptor 24 has a nine times greater area as compared with the operative plane area. However, the inverse square law has not been repealed for the secondary radiation or scatter that is generated close to the beam exit portal on the patient. The image acquisition geometry of the imaging system 10 suppresses scatter almost completely due to the huge air gap between the source of the scatter (the subject, table, etc.) and the image receptor 24.

The image receptor 24, while nine times greater in area, captures only a small fraction of all of the scattered radiation that would go to a traditional receptor if it were positioned proximate to the beam exit portal on the patient. Thus, the receptor 24 does not require an anti-scatter grid as found in most traditional systems. Because no radiation is lost to a scatter grid, there can be a net radiation dose reduction compared with the traditional technology. Moreover, by eliminating the grid, the image receptor 24 eliminates interfering moire patterns often imaged with grid-equipped matrix receptors.

Thus, image minifying system 10 puts the image receptor 24 a greater distance away from the anatomy than traditional x-ray systems, and at the same time provides state of the art image quality. In addition, the image minifying system 10 provides for the same dose rate, spatial resolution and the use of a "fractional" focal spot size range that permits practical high photon flux stop motion radiography with a penumbral unsharpness figure consistent with traditional geometry while the viewed and filmed images are displayed with a magnification within the traditional 1.2 to 1.4:1 ratio.

The image receptor 24 replaces the traditional intensifier or cassette, and utilizes the primary radiation as efficiently as traditional receptors. In addition the image receptor 24 has input dimensions large enough to capture all of the area of the much-magnified transmitted image. The image processing subsystem 40 electronically minifies and scan converts the already-captured magnified image so as to output the images to both viewing and recording devices in formats that simulate the traditional image acquired by a receptor positioned to capture anatomy at the typical 1.2 to 1.4:1 magnification ratio.

Referring now to FIGS. 3 and 4, there is shown an image minifying radiographic and fluoroscopic x-ray system 90 having an x-ray source 100 pivotally mounted to a rotatable platform 102 extending over or bridging a base 104 of a surgical table 106. The surgical table has a vertically adjustable, radiolucent, table surface 108. The x-ray source 100 is pivotally mounted to the platform 102 so that the x-ray source transmits an x-ray beam at a range of angles from about 45° to about 90° relative to the table surface 108. The surgical table 106, and more particularly the base 104, is movable relative to the platform 102 and x-ray source 100 by horizontally sliding the base 104 under the platform in directions normal to the vertical axis 114.

In the embodiment being described, the position of the platform 102, and hence the x-ray source 100, is fixed relative to the center of an overhead arcuate housing 112 along the vertical axis 114. That is, the axis of rotation of the platform 102, the azimuthal axis of rotation for the x-ray source 100, and the axis of rotation of the overhead arcuate housing 112, are all the vertical axis 114.

An amorphous silicon flat plate x-ray detector 110 is mounted within the arcuate housing 112. The housing 112 is supported by a rotatable mounting assembly which permits the housing 112, and hence the x-ray detector 110, to be rotated around the vertical axis 114 for alignment with the x-ray source 100. The arcuate shape of the housing 112 maintains a predetermined distance between detector 110 and the x-ray source 100 regardless of the position of detector 110 within the housing 112. Thus, a constant magnification ratio (e.g., 1:3) is maintained regardless of the position of the detector 110 and x-ray source 100, in the same manner as described above with regard to FIG. 1.

The x-ray detector 110 is motor driven within the curved housing 112. The housing 112 forms an arc segment suspended from the ceiling above the surgical table 106. The ends of the curved housing 112 terminate just above any standing personnel. An x-ray beam angulation signal is used to drive the x-ray detector 110 to a new position within the curved housing 112. The signal also causes a servo driven response to automatically angulate the x-ray source 100 (relative to the platform 102), so as to maintain x-ray beam alignment with the new position of the x-ray detector 110. Further, the x-ray source 100 and platform 102 are simultaneously driven so as to rotate azimuthally to maintain alignment with any commanded rotation of the curved housing about the vertical axis 114.

As previously mentioned, the x-ray source 102 is pivotally mounted to the platform 102 so that the x-ray source transmits an x-ray beam at any angle of up to about 45° relative to the surgical table surface 108. That is, when the x-ray source 100 is positioned directly beneath the table surface, an x-ray beam is projected along a path (e.g. the vertical axis 114) substantially normal or perpendicular to the plane of the surgical table. However, when desired, the x-ray source 100 is pivoted from directly under the surgical table so as to transmit an x-ray beam at any transverse angle in the range of up to about 45°, relative to the surgical table.

Referring now to FIG. 5, an image minifying radiographic and fluoroscopic x-ray system 140 has an x-ray source 142 pivotally mounted to a fixed platform. In particular, the x-ray source 142 is mounted to the platform so that the x-ray source transmits a transverse x-ray beam at any angle from about 0° to about 90° relative to a surgical table surface. That is, when the x-ray source is positioned directly beneath the table surface, the x-ray beam is projected along a path 143 substantially normal or perpendicular to the plane of the surgical table. However, when desired, the x-ray source 142 can be pivoted from directly under the surgical table so as to transmit an x-ray beam at any transverse angle in the range of about 0° to 90°.

As in the previous embodiments, the platform can extend over or bridge a base of a surgical table (not shown). The platform, and hence the x-ray source 142, rotates about a fixed vertical axis 143. The surgical table, and more particularly the base thereof, can be movable relative to the platform by horizontally sliding the base under the platform in directions normal to the vertical axis 143.

In order to achieve a full 90° angle relative to a surgical table, an amorphous silicon flat panel x-ray detector 144 is mounted to a movable arc segment 146 of a rotatable arcuate ceiling support 148. The arc segment 146 can be telescopically driven relative to the support 148 to align the x-ray detector 144 with the x-ray beam 152 transmitted from the x-ray source 142. The x-ray source 142 can be positioned at any angle between about 0° and about 90° relative to the surgical table. In the 0° position, the x-ray beam is transmitted substantially vertically along the axis 143. In the 90° position the x-ray beam is transmitted substantially horizontally along the path 150. In either case, the movable arc segment 146 can be manually or automatically driven to align the image receptor with the x-ray beam.

The curved housing 148 is dimensioned to clear standing personnel and includes curved rails (not shown) for directing movement of the smaller telescopic curved housing 146 which, in turn, directs the path of angulation of the motor-positioned x-ray detector 144 within the housing 146. The range of the servo driven response to an angulation command includes enough range to automatically angulate the x-ray beam to the horizontal.

As with the ceiling support 112, the arcuate shape of the ceiling support members 146, 148 serve to maintain a constant magnification ratio of the imaging subsystem regardless of the position of the x-ray source 142, in the same manner as described above with regard to FIGS. 3 and 4.

Referring now to FIG. 6, an image minifying radiographic and fluoroscopic x-ray system 160 has an x-ray source 162 fixedly mounted beneath a pivotal surgical table 164, and an amorphous silicon-based flat panel x-ray detector 166 fixedly mounted above the surgical table. The x-ray detector 166 can be secured to the surgical table by an extension arm 168. The surgical table 164, such as a urological surgery angulating table, is pivotal in the range of about 0° to about 90° (substantially horizontal to substantially vertical). The x-ray source 162 is mounted such that it transmits an x-ray beam 170 to the detector 166 along a path 172 that remains substantially normal to the surgical table 164 regardless of the position of the surgical table. That is, the surgical table 164, x-ray source 162 and receptor 166 all pivot together as a single unit.

The extension arm 168 maintains the x-ray detector 166 at a predetermined distance from the x-ray source 162 in order to maintain a constant magnification ratio of the imaging subsystem regardless of the position of the x-ray source 162, in the same manner as described above with regard to FIGS. 3–5.

What has been described is an image minifying radiographic and fluoroscopic x-ray system which includes an x-ray source assembly having an x-ray tube with a plurality of selectable size focal spots for fluoroscopy and radiography. The x-ray source is spaced from an object to be imaged by a first distance. An x-ray image receptor assembly is position at a second distance away from the object to be imaged. The second distance is greater than the first distance. A mechanism is provided for minifying projected image patterns received by the image receptor to a size for fluoroscopic viewing and radiographic and cineradiographic image recording that is approximately the size of the object being imaged so as to render displayed image patterns at a level of perceived detail that is substantially equal to non-minified images commonly acquired using x-ray receptors that are commonly positioned as close as practical to the object being imaged.

For instance, the image receptor assembly described above can include a large vacuum electronic x-ray image intensifier tube with its output phosphor coupled to a video camera that has its output coupled to a monitor for viewing and to a radiographic recording printer to accomplish simultaneous image minification by limiting the maximum size of the viewable and printed images.

In addition, an exemplary magnification ratio of 1:3 has been described. However, it is also contemplated that other magnification ratios can be implemented with the image minifying radiographic and fluoroscopic x-ray system embodiments described above.

It should be appreciated that applications outside of the field of health care such as, but not limited to, industrial inspection systems and airline baggage inspection can also benefit by removing the receptor from proximity with the object being examined.

The invention has been described with reference to the preferred embodiment(s). Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment(s), the invention is now claimed to be:

1. A diagnostic imaging system comprising:
    an x-ray tube source spaced from a plane of interest associated with an object to be imaged by a first fixed distance;
    an image receptor positioned at a second fixed distance away from said plane of interest associated with said object to be imaged remote from said x-ray tube, said second distance being greater than the first distance by a factor of 2.6 to 3.0; and
    means for minifying projected image patterns received by said image receptor by a factor of 1.4/2.6 to 1.2/3.0 to generate a human viewable display of a size that is about 1.0 to about 1.5 times the actual size of said object being imaged.

2. The imaging system of claim 1, further including a beam collimating device for controlling a size of an x-ray beam projected from said x-ray tube.

3. The imaging system of claim 1, further including means for varying the size of a focal spot of said x-ray tube.

4. The imaging system of claim 1, wherein said image receptor includes a flat panel x-ray detector.

5. The diagnostic imaging system of claim 4, wherein said flat plate x-ray detector is
    an amorphous silicon-based flat plate x-ray detector.

6. The imaging system of claim 1, wherein:
    said image receptor includes a flat plate x-ray detector, and
    said minifying means includes an image processor coupled to said flat plate x-ray detector which converts electronic image data from said amorphous silicon-based flat plate x-ray detector into an electronic image representation, and a minifying processor which scales the electronic image representation by a scaling factor for viewing on a display monitor.

7. The imaging system of claim 6, wherein said minifying processor includes an output coupled to electronic storage means.

8. The imaging system of claim 6, wherein said minifying processor includes an output coupled to a radiographic recording printer.

9. A diagnostic imaging system comprising:
    an x-ray tube source spaced from a plane of interest associated with an object to be imaged by a first distance;
    an image receptor positioned at a second distance away from said plane of interest associated with said object to be imaged remote from said x-ray tubes said second distance being greater than the first distance;
    means for minifying projected image patterns received by said image receptor to a size that is about the size of said object being imaged;
    a first motor for angulating the x-ray tube from a substantially vertical orientation;

an arcuate housing forming an arc segment, said image receptor being fully enclosed within said arcuate housing;

a second motor for driving said image receptor within said arcuate housing; and a motor control for controlling the first and second motors to coordinate angulating said x-ray tube and driving said image receptor within the arcuate housing.

10. The imaging system of claim 9, further including a rotatable mounting which supports said arcuate housing for rotation about a vertical axis.

11. A diagnostic imaging system comprising:

an x-ray tube source spaced from a plane of interest associated with an object to be imaged by a first distance;

an image receptor positioned at a second distance away from said plane of interest associated with said object to be imaged remote from said x-ray tube, said second distance being greater than the first distance;

means for minifying projected image patterns received by said image receptor to a size that is about the size of said object being imaged;

a first motor for angulating the x-ray tube from a substantially vertical orientation;

an arcuate housing forming an arc segment for retaining said image receptor therein;

a rotatable mounting which supports said arcuate housing for rotation about a vertical axis;

a second motor for driving said image receptor along said arcuate housing; and a motor control for controlling the first and second motors to coordinate angulating said x-ray tube and driving said image receptor along the arcuate housing, and for controlling rotation of said x-ray tube azimuthally to maintain alignment with a rotation of said arcuate housing about said vertical axis.

12. The imaging system of claim 9, wherein said arcuate housing includes a fixed portion and a telescopic portion which extends and retracts from said arcuate housing along an arcuate path, said image receptor being drivingly mounted to said telescopic portion.

13. The imaging system of claim 1, further including:

a fixed-length arm connected to a patient table at a pivot point of said fixed length arm, a first end of said arm being positioned closer to said pivot point than a second end of said arm, said x-ray tube being mounted to said first end of said fixed-length arm, and said image receptor being mounted to said second end of said arm, said arm being pivotally mounted to said patient table to rotate said x-ray tube and said image receptor together without relative movement therebetween.

14. A method of improving the resolution of a diagnostic image, comprising:

positioning an x-ray tube a first distance away from a plane of interest associated with an object to be imaged;

positioning an image receptor a second distance away from a plane of interest associated with said object to be imaged and opposite to said x-ray tube, said second distance being treater than the first distance by a factor of at least 2.6 such that x-ray image patterns projected on the image receptor are magnified; and minifying the magnified projected image patterns received by said image receptor by a factor of at least 1.4/2.6 to generate a human viewable display of a size that is approximately 1.0 times the size of said object being imaged.

15. The method of claim 14 further including:

adjusting an angular offset of (i) the x-ray tube to a vertical plane, and (ii) a radiation to electrical signal conversion plane of the image receptor relative to a horizontal plane.

16. The method of claim 14 further including:

adjusting cross sectional dimensions of a radiation beam generated by the x-ray tube.

17. The method of claim 14 further including:

rotating a radiation to electrical signal conversion plane of the image receptor around a central axis of an x-ray beam generated by the x-ray tube.

18. The method of claim 14 where in the positioning step includes positioning an amorphous silicon-based flat panel x-ray detector the second distance away from said object to be imaged.

19. A method of improving the resolution of a diagnostic image that is generated by a diagnostic imaging apparatus having a beam of radiation that is projected onto an x-ray detector, the beam of radiation is projected a first distance $D_1$ from a focal spot to a plane of a region of interest of a subject and a second distance $D_2$ from the region of interest plane to a conversion plane of the x-ray detector on which the radiation beam is converted into an electronic image representation, the electronic image representation being converted into a human readable display, and the x-ray detector having a resolution that is coarser than the human-readable display such that a magnification prior to detection and a subsequent minification of the electronic image representation improves an effective resolution of the diagnostic imaging apparatus, the method further including:

the distance $D_2$ being at least twice the distance $D_1$ such that each transverse dimension of the radiation beam at the conversion plane is $(D_1+D_2)/D_1$ as big as at the region of interest plane;

reducing the electronic image representation by between $D_1/(1.0(D_1+D_2))$ and $D_1/(1.5(D_1+D_2))$ such that each dimension of the human readable display is 1.0 to 1.5 times as large as corresponding structure intersected by the beam in the region of interest plane.

20. The method of claim 19 further including positioning an amorphous silicon-based flat panel x-ray detector along the conversion plane.

* * * * *